United States Patent
Parekh et al.

(10) Patent No.: US 9,481,961 B2
(45) Date of Patent: Nov. 1, 2016

(54) ANTIMICROBIAL FINISH ON FABRICS

(71) Applicant: Reliance Industries Ltd., Mumbai, Maharashtra (IN)

(72) Inventors: Anand Parekh, Ahmedabad, Gujarat (IN); Satya Pal Gomber, Ahmedabad, Gujarat (IN); Sujit Kumar Barik, Ahmedabad, Gujarat (IN)

(73) Assignee: RELIANCE INDUSTRIES LTD., Mumbai (IN)

( * ) Notice: Subject to any disclaimer, the term of this patent is extended or adjusted under 35 U.S.C. 154(b) by 0 days.

(21) Appl. No.: 14/949,154

(22) Filed: Nov. 23, 2015

(65) Prior Publication Data

US 2016/0138214 A1    May 19, 2016

Related U.S. Application Data

(62) Division of application No. 13/807,072, filed as application No. PCT/IN2011/000414 on Jun. 20, 2011, now abandoned.

(30) Foreign Application Priority Data

Jun. 29, 2010  (IN) ............... 1901MUM2010

(51) Int. Cl.
| | |
|---|---|
| D06M 13/152 | (2006.01) |
| D06M 13/00 | (2006.01) |
| D06M 13/144 | (2006.01) |
| D06M 13/156 | (2006.01) |
| D06M 15/263 | (2006.01) |
| D06M 15/643 | (2006.01) |
| D06M 16/00 | (2006.01) |
| D06C 29/00 | (2006.01) |
| A01N 25/34 | (2006.01) |
| A01N 31/08 | (2006.01) |

(52) U.S. Cl.
CPC ............ *D06M 13/152* (2013.01); *A01N 25/34* (2013.01); *A01N 31/08* (2013.01); *D06C 29/00* (2013.01); *D06M 13/005* (2013.01); *D06M 13/144* (2013.01); *D06M 13/156* (2013.01); *D06M 15/263* (2013.01); *D06M 15/6436* (2013.01); *D06M 16/00* (2013.01); *D06M 2200/01* (2013.01)

(58) Field of Classification Search
CPC .......... D06M 13/005; D06M 13/144; D06M 13/156; D06M 15/6436; D06M 15/263; D06M 16/00; D06M 13/152; D06M 2200/01; D06C 29/00; A01N 25/34; A01N 31/08
See application file for complete search history.

(56) References Cited

U.S. PATENT DOCUMENTS

| | | | | | |
|---|---|---|---|---|---|
| 3,699,958 | A | * | 10/1972 | Szucs | A61L 15/46 128/206.19 |
| 6,146,651 | A | * | 11/2000 | Kritzler | A01N 25/34 424/404 |
| 6,358,906 | B1 | * | 3/2002 | Ochs | A01N 25/02 510/130 |
| 6,368,361 | B1 | * | 4/2002 | Yayabe et al. | D06M 11/38 8/115.56 |
| 6,423,329 | B1 | | 7/2002 | Sine et al. | |
| 6,617,294 | B2 | | 9/2003 | Narula et al. | |
| 6,730,294 | B1 | * | 5/2004 | Kritzler | D06M 15/333 424/405 |
| 6,759,006 | B1 | * | 7/2004 | Siklosi et al. | A61L 2/07 422/1 |
| 6,780,799 | B2 | * | 8/2004 | Shalaby | A01N 25/10 442/123 |
| 6,821,936 | B2 | * | 11/2004 | Green et al. | A01N 25/34 252/8.82 |
| 6,946,433 | B2 | * | 9/2005 | Green et al. | A01N 25/34 252/8.82 |
| 7,081,139 | B2 | * | 7/2006 | Joerger et al. | A01N 43/16 424/443 |
| 7,232,777 | B1 | * | 6/2007 | Van Hyning | D06M 11/00 252/8.82 |
| 7,338,927 | B2 | * | 3/2008 | Shapiro | A01N 31/08 510/131 |
| 7,378,360 | B2 | | 5/2008 | Clark et al. | |
| 2005/0229327 | A1 | * | 10/2005 | Casella et al. | C11D 3/0015 8/115.51 |
| 2006/0204466 | A1 | * | 9/2006 | Littau | A01N 31/02 424/70.13 |
| 2008/0017068 | A1 | * | 1/2008 | Sokol | C08L 91/06 106/271 |
| 2008/0148491 | A1 | * | 6/2008 | van Buskirk | C11D 3/0015 8/103 |
| 2013/0095240 | A1 | * | 4/2013 | Parekh | D06M 13/005 427/223 |

FOREIGN PATENT DOCUMENTS

| | | | |
|---|---|---|---|
| CN | 1203293 A | | 12/1998 |
| CN | 1206293 A1 | * | 12/1998 |
| JP | 2004-84143 | | 3/2004 |
| JP | 2004-84143 A | * | 3/2004 |
| JP | 2007-290968 A | | 11/2007 |
| JP | 2007-290968 A | * | 11/2011 |

OTHER PUBLICATIONS

Kulinowski, Kristen M., Ph.D., "Environmental Impacts of Nanosilver," ICON Backgrounder—Nanosilver, Nov. 2008.

(Continued)

*Primary Examiner* — Anthony J Green
(74) *Attorney, Agent, or Firm* — Harness, Dickey & Pierce, P.L.C.

(57) ABSTRACT

A formulation is provided which comprises at least one phenolic compound in an amount of about 0.5 to about 1.2% of the mass of the formulation; at least one fragrance in an amount of about 0.3 to about 1.0% of the mass of the formulation; and at least one alcohol in an amount of about 90 to about 99% of the mass of the formulation. Said formulation is surfactant free and being capable of rendering anti-microbial finish to fabrics. And also, a process for preparing a fabric with anti-microbial finish is provided.

9 Claims, 1 Drawing Sheet

(56) References Cited

OTHER PUBLICATIONS

International Search Report, PCT/IN2001/000414, ISA/CN, Beijing, mailed Dec. 1, 2011.
H.D. Joshi et al. "Barrier Fabrics for Anti-microbial Protection." Research: Barrier Fabrics. International Dyer. May 2010.
European Search Report regarding Application No. 11800307.8-1303/2588662 PCT/IN2011000414, dated Nov. 7, 2013.
Office Action regarding U.S. Appl. No. 13/807,072, dated Aug. 21, 2015.
Office Action regarding U.S. Appl. No. 13/807,072, dated Apr. 29, 2015.
Office Action regarding U.S. Appl. No. 13/807,072, dated Jan. 16, 2015.
Restriction Requirement regarding U.S. Appl. No. 13/807,072, dated Sep. 22, 2014.

* cited by examiner

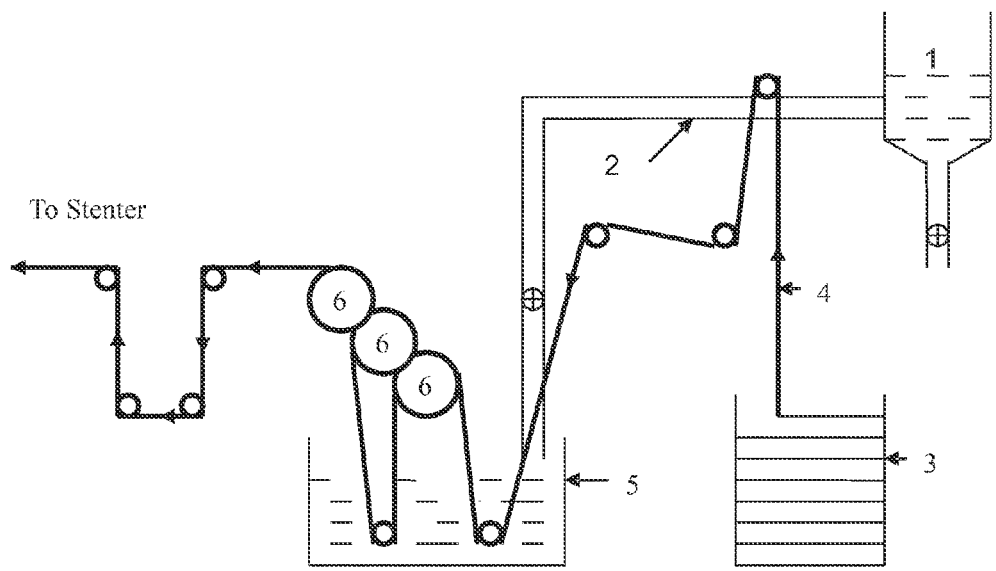

ANTIMICROBIAL FINISH ON FABRICS

CROSS-REFERENCE TO RELATED APPLICATIONS

This application is a continuation of United States patent application Ser. No. 13/807,072 filed on Dec. 27, 2012, now abandoned, which is a 371 U.S. National Stage of International Application No. PCT/IN2011/000414, filed Jun. 20, 2011, which claims the priority to Indian Patent Application No. 1901/MUM/2010, filed Jun. 29, 2010. The disclosures of the above applications are incorporated herein by reference.

FIELD OF INVENTION

The invention relates to an antimicrobial finish on the fabric.

This invention particularly envisages a durable antimicrobial finish and its application on the fabric.

BACKGROUND

Clothing and textile materials are not only carriers of microorganisms such as pathogenic bacteria, odor generating bacteria and mould fungi, but also good media for the growth of microorganisms. The inherent properties of the textile fibers provide room for the growth of micro-organisms. Humid and warm environment still aggravate the problem. Infestation by microbes cause cross infection by pathogens and development odor where the fabric is worn next to the skin. In addition, the staining and loss of the performance properties of textile substrates are the results of microbial attack. Obnoxious smell from the inner garments such as socks, spread of diseases, staining and degradation of textiles are some of the detrimental effects of bad microbes.

Though the use of antimicrobials have been known for the decades, it is only in the recent couple of years several attempts have been made on finishing textiles with antimicrobial compounds. Antimicrobial finish is a recent innovation in finishes. It also prevents garments from unpleasant odor.

The most common technology for making durable Antimicrobial apparel fabric is to introduce silver ion at the polymerization stage of the fibre manufacturing or to treat the fabric with nano-silver ions during finishing. But silver ion has many adverse effects on human being as well as on environment such as:

i) When human skin cells grown in a Petri-dish were exposed to nano-silver particles 7-20 nm in size, concentration dependent changes to cell morphology including abnormal size, shrinkage and rounded appearance were observed at concentrations above 6.25 microgm/ml.

ii) Nano silver has also some adverse effect on wound. After a week of treatment with a wound dressing impregnated with nano silver, the patient developed reversible sign of liver toxicity and a grayish dis-colouration of his face similar to that found in patient diagnosed with argyria.found. When wound dressing was removed, the clinical symptoms returned to normal in ten months.

iii) Nanosilver has recently been found at concentration as low as 0.14 micro gm/ml to be toxic to several species of nitrifying bacteria, which play an important role in the environment by converting ammonia in the soil to a form of nitrogen that can be used by plants. Increase in mass usage of Silver treated AMB fabric and the effluent generated during home laundering of garments may contaminate soil/water.

iv) Nanosilver's primary use as an antimicrobial has attracted the attention of the US Environment protection Agency which enforces the federal insecticides, Fungicide and Rodenticide Act (FIFRA). Also in Europe, the key question is whether nano-silver will be considered a new substance and therefore subjected to the rigorous notification procedure required under REACH law.

Nanosilver cannot be filtered out fully in Effluent Treatment Plant (ETP) and likely to cause soil and water contamination. Also the presence of Silver ion in the effluent water increases the load on Effluent treatment plant substantially. Nano-silver ion based AMB technology has been known to require several precautions in application as well as many costly modifications in effluent water treatment process.

(Ref:—*Environmental Impact of Nanosilver*—by Kristen M. Kulinowski, Ph. D—Nov. 18, -2008)

Apart from silver, antiseptics and disinfectants are extensively used in hospitals and other health care settings for a variety of topical and hard-surface applications. A wide variety of active chemical agents (biocides) are found in these products, many of which have been used for hundreds of years, including alcohols, phenols, iodine, and chlorine. Most of these active agents demonstrate broad-spectrum antimicrobial activity.

Chlorine- and iodine-based compounds are the most significant microbicidal halogens used in the clinic and have been traditionally used for both antiseptic and disinfectant purposes.

Chloro compounds such as Chloroxylenol is an effective antimicrobial agent. It is used as bacteriocidal, fungicidal and germicidal agent.

Many antimicrobial agents used in the textile industry are known from the food stuff and cosmetics sector. These substances are incorporated with textile substrates comparatively at lower concentrations. It must be ensured that these substances are not only permanently effective but also that they are compatible with skin and the environment.

Other chemical used for producing durable antimicrobial (AMB) fabric is 3-trimethoxy silyl propyl dimethyl octadecyl ammonium chloride—but it has also some disadvantages
  yellowing of the shade/colour of the fabric.
  it is a cationic compound—If any anionic detergent is used during home laundering, it will take out the cationic compound from the fabric making the antimicrobial effect less durable.

Following patents disclose anti-microbial fabrics and processes for preparing the same.

U.S. Pat. No. 3,699,958 disclose an antimicrobial woven or knitted fabric, characterized in that it is made using crimp yarn and is treated with cation-active antimicrobial compounds such as benzalkyl ammonium derivates, phenolic polyoxymethylene derivates.

U.S. Pat. No. 6,368,361 discloses a process for manufacturing an antibacterial fiber, characterized in that fiber is contacted with or immersed in an aqueous solution in which a cationic surfactant with a quaternary ammonium salt group, a water-soluble protein, and an alkaline compound are dissolved; and the fiber is separated from the aqueous solution and immersed in another aqueous solution containing tea polyphenol.

U.S. Pat. No. 6,780,799 discloses an antimicrobial nonwoven fabric comprising: a polymeric fiber substrate comprising phosphonic acid groups covalently bonded thereto and antimicrobial agents ionically bonded to the phosphonic acid groups. The antimicrobial agent used is benzalkonium chloride.

U.S. Pat. No. 6,821,936 discloses a wash durable antimicrobial treated substrate comprising an antimicrobial silver finish comprising silver zirconium phosphate compounds; at least one binder material selected from the group consisting of nonionic materials, anionic materials, and any mixtures thereof; and a substrate selected from the group consisting of a yarn, a fabric comprised of individual fibers, and a film;

U.S. Pat. No. 6,946,433 discloses a process for producing a wash durable antimicrobial treated substrate comprising an antimicrobial silver finish comprising compounds selected from the group consisting of silver-containing ion exchange compounds, silver-containing zeolites, silver-containing glass, and any mixtures thereof; and a substrate selected from the group consisting of a yarn, a fabric comprised of individual fibers, and a film.

U.S. Pat. No. 7,081,139 discloses antimicrobial polyester-containing articles (filament, fiber, yarn, fabric or film) and methodology for the preparation of antimicrobial polyester-containing articles utilizing chitosan and chitosan-metal complexes as the antimicrobial agent.

U.S. Pat. No. 7,232,777 discloses yarns and fabrics having a wash-durable antimicrobial silver particulate finish. It particularly disclose a treated substrate comprising a finish comprising a) solid compounds selected from the group consisting of metal particles, metal salts, metal oxides, and any combinations thereof, and b) at least one binder material selected from the group consisting of melamine-formaldehyde resins, acrylic resins, polyvinyl chloride/vinyl copolymers, and mixtures thereof: a substrate selected from the group consisting of a yarn, a fabric comprised of individual fibers, and a film.

U.S. Pat. No. 6146651 discloses a non-woven fabric treated with a biocidal composition, comprising: at least one halogenated phenolic biocide selected from the group consisting of pentachlorophenol (PCP), p-chloro-m-xylenol (PCMX), hexachlorophene, o-phenylphenol, dichlorophene, chlorophene, bromophene, trilosan and a combination thereof. ; a water soluble film forming polymer (polyvinylpyrrolidone polymer); and at least one surfactant.

The textile or fabrics containing antimicrobial agent disclosed in the above prior art does not provide effective and long lasting anti-microbial activity.

Thus, there is felt a need to develop antimicrobial finish on fabrics which is durable, completely safe for human being as well as for environment and does not alter the tone, colour and appearance of the fabric.

OBJECTS OF THE INVENTION

The main object of the invention is to provide a fabric with an anti-microbial property.

Another object of the present invention is to provide a fabric with an anti-microbial finish which is durable.

Yet, another object of the present invention is to provide a fabric with an anti-microbial finish which does not alter the tone, colour, hand feel and appearance of the fabric.

Yet, another object of the present invention is to provide an anti-microbial formulation which is safe for human being as well as for the environment.

Further object of the present invention is to provide a cost effective and environment friendly method of making anti-microbial fabric.

DEFINITIONS

As used in the present specification, the following words and phrases are generally intended to have the meanings as set forth below, except to the extent that the context in which they are used indicates otherwise.

Greige Fabric: The fabric which has not been subjected to washing or any chemical processing.

Scouring: It is a process in which the grey fabric is subjected to washing with the help of synthetic detergents and stain removers in order to remove dirt, dust, stains and various oily substances from the fabric and making it suitable for further chemical & mechanical processing.

Dyeing: It is a process where different types of dye stuffs are impregnated into the fabric in order to achieve the desired color.

Singeing: In this process the fabric is made to pass over a series of flames across the entire width to burn out the fibres protruding from the fabric surface. This is done to make the fabric surface smooth.

Crabbing: Crabbing sets the cloth and yarn twist by rotating the fabric over cylinders through a hot-water bath, or through a series of progressively hotter baths, followed by a cold-water bath. Crabbing is done to stabilize the fabric before dyeing and finishing and is necessary only for wool fabrics.

Heat Setting: It means a process of conferring stability upon fibres, yarns, or fabrics, by means of dry heat.

Shearing: In this process the fabric is passed over a set of rotating helical blades, across the width of the fabric to clean the surface hairs.

Decatising: Decatising is a finishing treatment whereby a fabric's physical and dimensional form is enhanced and then stabilized by the use of heat, moisture, pressure and time. Generally, a pressure decatising method produces a permanent change in fabric properties by the action of heat and pressurized steam at greater than 100 kPa (1 atm) pressure on a mechanically constrained fabric, and is usually performed during the final stages of fabric production for several reasons: (a) to develop desirable aesthetic qualities in the fabric such as handle, luster and smoothness, (b) to improve the dimensional stability of the fabric particularly for purposes of garment assembly, (c) to permanently set or preserve these qualities during fabric use.

Pick-up %: It is the quantity of the solution absorbed by the fabric after squeezing, expressed as the percentage to the weight of the dry fabric. Pick-up % is calculated as below $$\text{Pick-up \%} = \frac{\left(\begin{array}{c}GSM \text{ of the wet fabric after squeezing} -\\ GSM \text{ of Fabric before application}\end{array}\right) \times 100}{GSM \text{ of Fabric before application}}$$

GSM—Grams per square meter
Gpl—Grams/Liter
Stenter—Stenter is an open width finishing machine where the fabric passes through a set of chambers, with provision of hot air blowing. This machine can be used for drying and heat setting of fabric.
PV: Polyester/Viscose
PW: Polyester/Wool

SUMMARY OF THE INVENTION

In accordance with the present invention there is provided a formulation comprising:
at least one phenolic compound in an amount of about 0.5 to about 1.2% of the mass of the formulation;
at least one fragrance in an amount of about 0.3 to about 1.0% of the mass of the formulation; and at least one alcohol in an amount of about 90 to about 99% of the mass of the formulation,
said formulation being surfactant free and being capable of rendering anti-microbial finish to fabrics.

Typically, the phenolic compound is selected from the group consisting of 2-chloro-5-hydroxy-1,3-dimethylbenzene; 2-chloro-5-hydroxy-m-xylene; 4-chloro-3,5-xylenol; 4-chloro-3,5-dimethylphenol; 4-chloro-5,3-dimethylphenol; 4-chloro-m-xylenol; p-chloro-3,5-xylenol and p-chloro-m-xylenol.

Preferably, the phenolic compound is chloroxylenol.

Typically, the fragrance is 2-(4-Methyl-1-cyclohex-3-enyl) propan-2-ol (Terpineol).

Preferably, the alcohol is isopropanol.

Typically, the fabric is selected from the group consisting of wool, cotton, silk, linen, hemp, ramie, jute, rayon, nylon, polyester, aramid, acrylic, spandex, olefin fibre, polyester viscose, polyester wool, modacrylic olefin acrylic polyester, PTFE, PP, PPE, carbon fiber, vinylon, SARAN™ polyvinylidene chloride (PVDC), vinalon, MODAL® cellulose fiber, SULFAR™ polysulfide fiber, polybenzimidazole fibre, PLA, lyocell, ORLON® acrylic fiber, VECTRAN® liquid crystal polymer (LCP), ZYLON® acrylonitrile and combinations thereof.

In accordance with another aspect of the present invention there is provided a process for preparing fabric with anti-microbial finish; said process comprising the following steps:

(a) providing a fabric selecting from the group consisting of wool, cotton, silk, linen, hemp, ramie, jute, rayon, nylon, polyester, aramid, acrylic, spandex, olefin fibre, polyester viscose, polyester wool, modacrylic olefin acrylic polyester, PTFE, PP, PPE, carbon fiber, vinylon, SARAN™ polyvinylidene chloride (PVDC), vinalon, MODAL® cellulose fiber, SULFAR™ polysulfide fiber, polybenzimidazole fibre, PLA, lyocell, ORLON® acrylic fiber, VECTRAN® liquid crystal polymer (LCP), ZYLON® acrylonitrile and combinations thereof;

(b) subjecting the fabric to pre-treatment;

(c) providing an anti-microbial finish formulation comprising i) at least one phenolic compound in an amount of about 0.5 to about 1.2% of the mass of the formulation, ii) at least one fragrance in an amount of about 0.3 to about 1.0% of the mass of the formulation, and iii) at least one alcohol alcohol in an amount of about 90 to about 99% of the mass of the formulation;

(d) applying said formulation onto the pre-treated fabric at a temperature of about 25 to 50° C.; and (e) subjecting the fabric to post-treatment to obtain a fabric with anti-microbial finish.

Typically, the pre-treatment comprises at least one operation selected from the group consisting of scouring at a temperature of about 55-60° C., drying at a temperature of about 90-160° C., heat setting on stenter at a temperature of about 170-210° C., dyeing, singeing, crabbing and shearing.

Typically, the post-treatment comprises at least one operation selected from the group consisting of drying at a temperature of about 90-160° C., pressing and kier decasting at a temperature of about 100-115° C.

In accordance with another embodiment of the present invention the process further comprising a step of incorporating at least one chemical selected from the group consisting of acrylic co-polymer and micro amino silicone into the fabric before the post-treatment step.

BRIEF DESCRIPTION OF THE DRAWING

The invention will now be described with reference to the accompanying drawing in which:

FIG. 1 illustrates a process for preparing a fabric with anti-microbial finish.

DETAILED DESCRIPTION OF THE INVENTION

In accordance with the present invention there is provided a formulation comprising:
at least one phenolic compound in an amount of about 0.5 to about 1.2% of the mass of the formulation;
at least one fragrance in an amount of about 0.3 to about 1.0% of the mass of the formulation; and
at least one alcohol in an amount of about 90 to about 99% of the mass of the formulation,
said formulation being surfactant free and being capable of rendering anti-microbial finish to fabrics.

In accordance with the present invention the phenolic compound is used as anti-microbial agent and which is selected from the group consisting of 2-chloro-5-hydroxy-1,3-dimethylbenzene; 2-chloro-5-hydroxy-m-xylene; 4-chloro-3,5-xylenol; 4-chloro-3,5-dimethylphenol; 4-chloro-5,3-dimethylphenol; 4-chloro-m-xylenol; p-chloro-3,5-xylenol and p-chloro-m-xylenol.

Preferably, the phenolic compound is chloroxylenol.

Typically, the fragrance is 2-(4-Methyl-1-cyclohex-3-enyl) propan-2-ol (Terpineol).

Preferably, the alcohol is isopropanol.

In accordance with the present invention the fabric is selected from the group consisting of wool, cotton, silk, linen, hemp, ramie, jute, rayon, nylon, polyester, aramid, acrylic, spandex, olefin fibre, polyester viscose, polyester wool, modacrylic olefin acrylic polyester, PTFE, PP, PPE, carbon fiber, vinylon, SARAN™ polyvinylidene chloride (PVDC), vinalon, MODAL® cellulose fiber, SULFAR™ polysulfide fiber, polybenzimidazole fibre, PLA, lyocell, ORLON® acrylic fiber, VECTRAN® liquid crystal polymer (LCP) ZYLON® acrylonitrile and combinations thereof.

In accordance with another aspect of the present invention there is provided a process for preparing a fabric with anti-microbial finish. The process of the present invention is described herein below.

The first step is providing a fabric selecting from the group consisting of wool, cotton, silk, linen, hemp, ramie, jute, rayon, nylon, polyester, aramid, acrylic, spandex, olefin fibre, polyester viscose, polyester wool, modacrylic olefin acrylic polyester, PTFE, PP, PPE, carbon fiber, vinylon, SARAN™ polyvinylidene chloride (PVDC), vinalon, MODAL® cellulose fiber, SULFAR™ polysulfide fiber, polybenzimidazole fibre, PLA, lyocell, ORLON® acrylic fiber, VECTRAN® liquid crystal polymer (LCP), ZYLON® acrylonitrile and combinations thereof.

Then the selected fabric is subjected to pre-treatment. Typically, the pre-treatment comprises at least one operation selected from the group consisting of scouring at a temperature of about 55-60° C., drying at a temperature of about 90-160° C., heat setting on stenter at a temperature of about 170-210° C., dyeing, singeing, crabbing and shearing.

In the next step, an anti-microbial finish formulation in accordance with the present invention is prepared. Typically, the anti-microbial finish formulation comprises i) at least one phenolic compound in an amount of about 0.5 to about 1.2% of the mass of the formulation, ii) at least one fragrance in an amount of about 0.3 to about 1.0% of the mass of the formulation, and iii) at least one alcohol in an amount of about 90 to about 99% of the mass of the formulation.

The prepared anti-microbial finish formulation is then applied onto the pre-treated fabric at a temperature of about 25 to 50° C. Finally, the fabric is subjected to post-treatment to obtain a fabric with anti-microbial finish. Typically, the post-treatment comprises at least one operation selected from the group consisting of drying at a temperature of about 90-160° C., pressing and kier decatising at a temperature of about 100-115° C.

In accordance with another embodiment of the present invention the process further comprising a step of incorporating at least one chemical selected from the group consisting of acrylic co-polymer and micro amino silicone into the fabric before the post-treatment step.

In accordance with one embodiment of the present invention, the process is further described with the help of a FIGURE (FIG. 1). Typically, the assembly used in the process for the preparation of anti-microbial fabric in accordance with the present invention comprises: finishing tank (1), pipe (2) for feeding the solution from tank to mangle, fabric trolley (3), mangle (5), squeeze rollers (6) and stenter. Initially, the anti-microbial formulation of the present invention & binder are added in a finishing Tank (1) along with normal finishing chemicals. The final solution goes to the mangle (5) through a pipe (2) for padding where fabric (4) picks up the solution and the fabric passes through a set of squeezing rollers (6) to squeeze the excess solution.

The pickup is about 55% to 70%. After this, fabric enters into a heating chamber of stenter for drying.

The invention will now be described with respect to the following examples which does not limit the invention in any way and only exemplify the invention.

EXAMPLE 1

Preparation of Anti-Microbial Formulation (a)

The anti-microbial formulation was prepared using the following ingredients.

| Sr. No. | Ingredients | Quantity |
|---|---|---|
| 1 | Isopropyl alcohol | 985 ml |
| 2 | chloroxylenol | 12 gm |
| 3 | Terpineol | 3 ml |

EXAMPLE 2

Preparation of Anti-Microbial Formulation (b)

The anti-microbial formulation was prepared using the following ingredients.

| Sr. No. | Ingredients | Quantity |
|---|---|---|
| 1 | Isopropyl alcohol | 985 ml |
| 2 | chloroxylenol | 10 gm |
| 3 | Terpineol | 5 ml |

EXAMPLE 3

Preparation of Anti-Microbial Formulation (c)

The anti-microbial formulation was prepared using the following ingredients.

| Sr. No. | Ingredients | Quantity |
|---|---|---|
| 1 | Isopropyl alcohol | 985 ml |
| 2 | chloroxylenol | 8 gm |
| 3 | Terpineol | 7 ml |

EXAMPLE 4

Preparation of Anti-Microbial Formulation (d)

The anti-microbial formulation was prepared using the following ingredients.

| Sr. No. | Ingredients | Quantity |
|---|---|---|
| 1 | Isopropyl alcohol | 985 ml |
| 2 | chloroxylenol | 5 gm |
| 3 | Terpineol | 10 ml |

The formulations prepared as per examples 1 to 4 were used for the preparation of anti-microbial fabrics of different types. Typically, the formulation is used in an amount of about 10 to 25 gram per liter.

EXAMPLE 5

Preparation of Anti-Microbial Fabrics of Different Types

The anti-microbial fabrics of different types were prepared using the process steps described in table No. 1.

TABLE NO. 1

| | | Processing steps for preparation of anti-microbial fabrics | | | | | |
|---|---|---|---|---|---|---|---|
| Sr. No. | Process | Polyester/Cellulosic - Suiting/Shirting Fabric (1) | 100% Polyester & Polyester/Cellulosic - Piece Dyed Suiting/Shirting Fabric (2) | PW - Suiting Fabric (3) | 100% Wool - Suiting Fabric (4) | 100% Polyester Auto textiles- Piece Dyed Fabric (5) | 100% Polyester Auto textiles- Yarn Dyed Fabric (6) |
| 1 | Scouring | 55-60° C. | 55-60° C. | 55-60° C. | 55-60° C. | 55-60° C. | 55-60° C. |
| 2 | Drying | 90-160° C. | 90-160° C. | 90-160° C. | 90-160° C. | 90-160° C. | 90-160° C. |
| 3 | Heat setting on Stenter | 170-210° C. | 170-210° C. | 170-210° C. | — | 170-210° C. | 170-210° C. |

TABLE NO. 1-continued

Processing steps for preparation of anti-microbial fabrics

| Sr. No. | Process | Polyester/ Cellulosic - Suiting/Shirting Fabric (1) | 100% Polyester & Polyester/ Cellulosic - Piece Dyed Suiting/Shirting Fabric (2) | PW - Suiting Fabric (3) | 100% Wool - Suiting Fabric (4) | 100% Polyester Auto textiles- Piece Dyed Fabric (5) | 100% Polyester Auto textiles- Yarn Dyed Fabric (6) |
|---|---|---|---|---|---|---|---|
| 4 | Dyeing | — | Max upto 135° C. | — | — | Max upto 135° C. | |
| 5 | Drying | — | 90-160° C. | — | — | 90-160° C. | |
| 6 | Singeing | 80-120 Mtr/min | 80-120 Mtr/min | 80-120 Mtr/min | 80-120 Mtr/min | — | |
| 7 | Crabbing | — | — | — | 110-130° C. | — | |
| 8 | Scouring | 55-60° C. | 55-60° C. | 55-60° C. | 55-60° C. | — | |
| 9 | Drying | 90-160° C. | 90-160° C. | 90-160° C. | 90-160° C. | — | |
| 10 | Shearing | — | — | 15-30 mtr/min | 15-30 mtr/min | — | |
| 11 | Chemical Application | | | | | | |
| 11.1 | Basic Formulation | 10-25 gpl | 10-25 gpl | 10-25 gpl | 10-25 gpl | 10-25 gpl | 10-25 gpl |
| 11.2 | Acrylic co-polymer | 5-15 gpl | 5-15 gpl | 5-15 gpl | | 5-15 gpl | 5-15 gpl |
| 11.3 | Micro Amino Silicone | — | — | 1-5 gpl | 1-5 gpl | — | — |
| 11.4 | Drying | 90-160° C. | 90-160° C. | 90-160° C. | 90-160° C. | 90-160° C. | 90-160° C. |
| 12 | 1$^{St}$ pressing | 15-30 mtr/min | 15-30 mtr/min | 15-30 mtr/min | 15-30 mtr/min | | |
| 13 | Kier Decatising | 100-115° C., Pressure 0.4-1.2 Bar | 100-115° C., Pressure 0.4-1.2 Bar | 100-115° C., Pressure 0.4-1.2 Bar | 100-115° C., Pressure 0.4-1.2 Bar | | |
| 14 | Final Pressing | 15-30 mtr/min | 15-30 mtr/min | 15-30 mtr/min | 15-30 mtr/min | | |

EXAMPLE 6

Anti-Microbial Testing

The fabrics prepared in accordance with the present invention were tested for anti-microbial activity using standard AATCC-147-2004 method.
The results are shown in following Table No. 2.

| Product | Condition | Formulation | Test Organism | Zone of Inhibition | Growth Under Specimen | Conclusion | Test Status |
|---|---|---|---|---|---|---|---|
| PV Suiting/ Shirting Fabric | Initial | a | Staph. Aureus | 2.4 mms | No Growth | Diffusible | Pass |
| | | | K. Pneumoniae | 1.0 mm | No Growth | | |
| | | b | Staph. Aureus | 1.0 mm | No Growth | Diffusible | Pass |
| | | | K. Pneumoniae | 4.2 mm | No Growth | | |
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |
| | | e | Staph. Aureus | No Zone | No Growth | Bacteriostatic | Pass |
| | | | K. Pneumoniae | No Zone | No Growth | | |
| PV Suiting/ Shirting Fabric | After 100 Washes | a | Staph. Aureus | No Zone | No Growth | Bacteriostatic | Pass |
| | | | K. Pneumoniae | No Zone | No Growth | | |
| | | b | Staph. Aureus | No Zone | No Growth | Bacteriostatic | Pass |
| | | | K. Pneumoniae | No Zone | No Growth | | |
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |
| | | e | Staph. Aureus | No Zone | No Growth | Bacteriostatic | Pass |
| | | | K. Pneumoniae | No Zone | No Growth | | |
| 100% Polyester & PV Piece dyed Fabric | Initial | a | Staph. Aureus | 5.6 mms | No Growth | Diffusible | Pass |
| | | | K. Pneumoniae | 2.2 mms | No Growth | | |
| | | b | Staph. Aureus | 3.5 mms | No Growth | Diffusible | Pass |
| | | | K. Pneumoniae | 2.1 mms | No Growth | | |

-continued

| Product | Condition | Formu-lation | Test Organism | Zone of Inhibition | Growth Under Specimen | Conclusion | Test Status |
|---|---|---|---|---|---|---|---|
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |
| | | e | Staph. Aureus | No Zone | No Growth | Bacteriostatic | Pass |
| | | | K. Pneumoniae | No Zone | No Growth | | |
| 100% Polyester & PV Piece dyed Fabric | After 100 Washes | a | Staph. Aureus | 2.0 mms | No Growth | Diffusible | Pass |
| | | | K. Pneumoniae | No Zone | No Growth | | |
| | | b | Staph. Aureus | No Zone | No Growth | Bacteriostatic | Pass |
| | | | K. Pneumoniae | No Zone | No Growth | | |
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |
| | | e | Staph. Aureus | No Zone | No Growth | Bacteriostatic | Pass |
| | | | K. Pneumoniae | No Zone | No Growth | | |
| PW Suiting Fabric | Initial | a | Staph. Aureus | 1.0 mms | No Growth | Diffusible | Pass |
| | | | K. Pneumoniae | No Zone | No Growth | | |
| | | b | Staph. Aureus | 0.5 mms | No Growth | Diffusible | Pass |
| | | | K. Pneumoniae | No Zone | No Growth | | |
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |
| | | e | Staph. Aureus | No Zone | No Growth | Bacteriostatic | Pass |
| | | | K. Pneumoniae | No Zone | No Growth | | |
| PW Suiting Fabric | After 100 Washes | a | Staph. Aureus | No Zone | No Growth | Bacteriostatic | Pass |
| | | | K. Pneumoniae | No Zone | No Growth | | |
| | | b | Staph. Aureus | No Zone | No Growth | Bacteriostatic | Pass |
| | | | K. Pneumoniae | No Zone | No Growth | | |
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |
| | | e | Staph. Aureus | No Zone | No Growth | Bacteriostatic | Pass |
| | | | K. Pneumoniae | No Zone | No Growth | | |
| 100% Wool Suiting Fabric | Initial | a | Staph. Aureus | No Zone | No Growth | Bacteriostatic | Pass |
| | | | K. Pneumoniae | No Zone | No Growth | | |
| | | b | Staph. Aureus | No Zone | No Growth | Bacteriostatic | Pass |
| | | | K. Pneumoniae | No Zone | No Growth | | |
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |
| | | e | Staph. Aureus | No Zone | No Growth | Bacteriostatic | Pass |
| | | | K. Pneumoniae | No Zone | No Growth | | |
| 100% Wool Suiting Fabric | After 20 Dry clean | a | Staph. Aureus | No Zone | No Growth | Bacteriostatic | Pass |
| | | | K. Pneumoniae | No Zone | No Growth | | |
| | | b | Staph. Aureus | No Zone | No Growth | Bacteriostatic | Pass |
| | | | K. Pneumoniae | No Zone | No Growth | | |
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |
| | | e | Staph. Aureus | No Zone | No Growth | Bacteriostatic | Pass |
| | | | K. Pneumoniae | No Zone | No Growth | | |
| 100% Polyester Auto Textiles Piece dyed Fabric | Initial | a | Staph. Aureus | No Zone | No Growth | Bacteriostatic | Pass |
| | | | K. Pneumoniae | No Zone | No Growth | | |
| | | b | Staph. Aureus | No Zone | No Growth | Bacteriostatic | Pass |
| | | | K. Pneumoniae | No Zone | No Growth | | |
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |
| | | e | Staph. Aureus | No Zone | No Growth | Bacteriostatic | Pass |
| | | | K. Pneumoniae | No Zone | No Growth | | |
| 100% Polyester Auto Textiles Piece dyed Fabric | After 1000 Cycle Taber Abrasion | a | Staph. Aureus | No Zone | No Growth | Bacteriostatic | Pass |
| | | | K. Pneumoniae | No Zone | No Growth | | |
| | | b | Staph. Aureus | No Zone | No Growth | Bacteriostatic | Pass |
| | | | K. Pneumoniae | No Zone | No Growth | | |
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |

| Product | Condition | Formulation | Test Organism | Zone of Inhibition | Growth Under Specimen | Conclusion | Test Status |
|---|---|---|---|---|---|---|---|
| | | e | Staph. Aureus | No Zone | No Growth | Bacteriostatic | Pass |
| | | | K. Pneumoniae | No Zone | No Growth | | |
| 100% Polyester Auto Textiles Yarn dyed Fabric | Initial | a | Staph. Aureus | No Zone | No Growth | Bacteriostatic | Pass |
| | | | K. Pneumoniae | No Zone | No Growth | | |
| | | b | Staph. Aureus | No Zone | No Growth | Bacteriostatic | Pass |
| | | | K. Pneumoniae | No Zone | No Growth | | |
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |
| | | e | Staph. Aureus | No Zone | No Growth | Bacteriostatic | Pass |
| | | | K. Pneumoniae | No Zone | No Growth | | |
| 100% Polyester Auto Textiles Yarn dyed Fabric | After 1000 Cycle Taber Abrasion | a | Staph. Aureus | No Zone | No Growth | Bacteriostatic | Pass |
| | | | K. Pneumoniae | No Zone | No Growth | | |
| | | b | Staph. Aureus | No Zone | No Growth | Bacteriostatic | Pass |
| | | | K. Pneumoniae | No Zone | No Growth | | |
| | | c | Staph. Aureus | No Zone | No Growth | Bacteriostatic | Pass |
| | | | K. Pneumoniae | No Zone | No Growth | | |
| | | d | Staph. Aureus | No Zone | No Growth | Bacteriostatic | Pass |
| | | | K. Pneumoniae | No Zone | No Growth | | |
| | | e | Staph. Aureus | No Zone | No Growth | Bacteriostatic | Pass |
| | | | K. Pneumoniae | No Zone | No Growth | | |

From the results as shown in above table it is clear that all the fabrics, treated with all five formulations possess anti-microbial property at initial condition and after 100 washes/20 dry cleanings (in case of all wool fabrics) as well.

The fabrics prepared in accordance with the present invention show bacteriostatic property or diffusible anti microbial property.

Technical Advancement and Economic Significance:

The fabric with an anti-microbial finish of the present invention is durable up to 100 home launderings as well as to various abrasion and weathering conditions.

The chemicals used in the formulation are completely safe for human being as well as for environment. The anti-microbial formulation is also non-cytotoxic as tested by test method no. ISO 10993-5: 2009.

Application of anti-microbial finish does not require any change in the normal processing sequence of the fabrics. Anti-microbial formulation is added along with normal finish at chemical finishing stage in the processing sequence. It is compatible with all the normal finishes applied to fabrics.

It does not alter the tone, color, hand-feel and appearance of the fabric, which is of very high importance in consumer and apparel fabrics.

It is the most cost effective method of making durable anti microbial apparel fabric which can be used for the masses.

Application of this technology, using anti-microbial formulation does not require any alteration, whatsoever in the effluent water treatment procedure/process. It does not add any additional burden—process wise as well as cost wise.

The numerical values mentioned for the various physical parameters, dimensions or quantities are only approximations and it is envisaged that the values higher/lower than the numerical values assigned to the parameters, dimensions or quantities fall within the scope of the invention, unless there is a statement in the specification specific to the contrary.

While considerable emphasis has been placed herein on the specific features of the preferred embodiment, it will be appreciated that many additional features can be added and that many changes can be made in the preferred embodiment without departing from the principles of the invention. These and other changes in the preferred embodiment of the invention will be apparent to those skilled in the art from the disclosure herein, whereby it is to be distinctly understood that the foregoing descriptive matter is to be interpreted merely as illustrative of the invention and not as a limitation.

The invention claimed is:

1. A process for preparing a fabric with anti-microbial finish; said process comprising the following steps:
   a. providing a fabric selected from the group consisting of wool, rayon, polyester, polyester viscose, polyester wool and combinations thereof;
   b. subjecting the fabric to a step of pre-treatment;
   c. mixing together:
      i. at least one phenolic compound in an amount of about 0.5 to about 1.2% of the mass of the formulation;
      ii. at least one fragrance in an amount of about 0.3 to about 1.0% of the mass of the formulation; and
      iii. at least one alcohol in an amount of about 90 to about 99% of the mass of the formulation,
      to form an anti-microbial finish formulation;
   d. forming a mixture by mixing 10 to 25 gpl of said anti-microbial finish formulation with 5 to 15 gpl of acrylic co-polymer;
   e. transferring said mixture to a reaction vessel and applying said mixture onto said pre-treated fabric at a temperature of about 25 to 50° C.; and
   f. subjecting said fabric to a step of post-treatment to obtain a fabric with anti-microbial finish.

2. The process as claimed in claim 1, wherein said step of pre-treatment (b) is selected from the group consisting of scouring at a temperature of about 55-60° C., dyeing, singeing, crabbing and shearing.

3. The process as claimed in claim 1, wherein said step of post-treatment (f) is selected from the group consisting of drying at a temperature of about 90-160° C., pressing and decatising.

4. The process as claimed in claim 1, wherein the forming a mixture further comprises mixing 1 to 5 gpl of micro amino silicone with the anti-microbial finish and the acrylic co-polymer.

5. The process as claimed in claim 1, wherein the phenolic compound is selected from the group consisting of 2-chloro-5-hydroxy-1,3-dimethylbenzene; 2-chloro-5-hydroxy-m-xylene; 4-chloro-3,5-xylenol; 4-chloro-3,5-dimethylphenol; 4-chloro-m-xylenol; p-chloro-3,5-xylenol and p-chloro-m-xylenol.

6. The process as claimed in claim 1, wherein the phenolic compound is chloroxylenol.

7. The process as claimed in claim 1, wherein the fragrance is 2-(4-Methyl-1-cyclohex-3-enyl) propan-2-ol(Terpineol).

8. The process as claimed in claim 1, wherein the alcohol is isopropanol.

9. A fabric with an anti-microbial finish prepared by the process as claimed in claim 1, said fabric being capable of retaining anti-microbial properties up to 100 launderings as tested by test protocol AATCC-147.

* * * * *